(12) United States Patent
Feld et al.

(10) Patent No.: US 9,114,033 B2
(45) Date of Patent: Aug. 25, 2015

(54) STENT WITH SELF-DEPLOYABLE PORTION

(75) Inventors: Tanhum Feld, Moshav Merhavya (IL); Eitan Konstantino, Orinda, CA (US)

(73) Assignee: TRIREME MEDICAL, INC., Pleasanton, CA (US)

( * ) Notice: Subject to any disclaimer, the term of this patent is extended or adjusted under 35 U.S.C. 154(b) by 1728 days.

(21) Appl. No.: 11/330,382

(22) Filed: Jan. 10, 2006

(65) Prior Publication Data
US 2006/0173528 A1    Aug. 3, 2006

Related U.S. Application Data

(60) Provisional application No. 60/740,935, filed on Nov. 29, 2005, provisional application No. 60/712,949, filed on Aug. 30, 2005, provisional application No. 60/684,454, filed on May 24, 2005, provisional application No. 60/643,062, filed on Jan. 10, 2005.

(51) Int. Cl.
*A61F 2/06* (2013.01)
*A61F 2/856* (2013.01)
*A61F 2/91* (2013.01)
(Continued)

(52) U.S. Cl.
CPC . *A61F 2/856* (2013.01); *A61F 2/91* (2013.01); *A61F 2/915* (2013.01); *A61F 2/954* (2013.01); *A61F 2/958* (2013.01); *A61F 2002/821* (2013.01); *A61F 2002/9155* (2013.01); *A61F 2002/91508* (2013.01); *A61F 2002/91516* (2013.01); *A61F 2002/91525* (2013.01); *A61F 2002/91533* (2013.01); *A61F 2002/91558* (2013.01)

(58) Field of Classification Search
CPC ............ A61F 2002/91508; A61F 2002/91516; A61F 2002/91525; A61F 2/856; A61F 2/91; A61F 2/915
USPC ....................................... 623/1.31, 1.15, 1.35
See application file for complete search history.

(56) References Cited

U.S. PATENT DOCUMENTS 4,994,071 A    2/1991   MacGregor
5,147,332 A    9/1992   Moorehead
(Continued)

FOREIGN PATENT DOCUMENTS

DE     29 708 803 U1    7/1997
DE     29 701 758 U1    3/1999
(Continued)

OTHER PUBLICATIONS

Supplementary Search Report of EP Application No. 06718033, dated Mar. 12, 2008, 5 pages total.
(Continued)

*Primary Examiner* — Kathleen Holwerda
*Assistant Examiner* — Sarah Simpson
(74) *Attorney, Agent, or Firm* — Wilson Sonsini Goodrich & Rosati

(57) ABSTRACT

The present invention provides methods and devices for placement of a stent in a bifurcation or ostial lesion. The stent comprises a main body and a flaring portion. The main body is designed to expand and support a main vessel while the flaring portion deploys at least partially in response to expansion of the main body and is designed to open into and support a side branch or bifurcation ostium area. The stent may also comprise a therapeutic agent which can be delivered to a blood vessel.

11 Claims, 17 Drawing Sheets

(51) Int. Cl.
*A61F 2/915* (2013.01)
*A61F 2/954* (2013.01)
*A61F 2/958* (2013.01)
*A61F 2/82* (2013.01)

(56) References Cited

U.S. PATENT DOCUMENTS

| | | | |
|---|---|---|---|
| 5,607,444 A | 3/1997 | Lam | |
| 5,609,627 A | 3/1997 | Goicoechea et al. | |
| 5,749,825 A | 5/1998 | Fischell et al. | |
| 5,755,735 A | 5/1998 | Richter et al. | |
| 5,827,229 A | 10/1998 | Auth et al. | |
| 5,868,777 A | 2/1999 | Lam | |
| 5,882,329 A | 3/1999 | Patterson et al. | |
| 5,928,248 A | 7/1999 | Acker | |
| 6,048,361 A | 4/2000 | Von Oepen | |
| 6,099,497 A | 8/2000 | Adams et al. | |
| 6,165,195 A | 12/2000 | Wilson et al. | |
| 6,210,429 B1 | 4/2001 | Vardi et al. | |
| 6,221,098 B1 | 4/2001 | Wilson et al. | |
| 6,293,964 B1* | 9/2001 | Yadav | 623/1.11 |
| 6,325,826 B1 | 12/2001 | Vardi et al. | |
| 6,579,309 B1* | 6/2003 | Loos et al. | 623/1.16 |
| 6,596,011 B2 | 7/2003 | Johnson et al. | |
| 6,596,020 B2 | 7/2003 | Vardi et al. | |
| 6,599,316 B2 | 7/2003 | Vardi et al. | |
| 6,676,691 B1 | 1/2004 | Hosny | |
| 6,682,536 B2 | 1/2004 | Vardi et al. | |
| 6,689,156 B1 | 2/2004 | Davidson et al. | |
| 6,692,483 B2 | 2/2004 | Vardi et al. | |
| 6,706,062 B2 | 3/2004 | Vardi et al. | |
| 6,709,440 B2 | 3/2004 | Callol et al. | |
| 6,835,203 B1 | 12/2004 | Vardi et al. | |
| 6,884,258 B2 | 4/2005 | Vardi et al. | |
| 2002/0042650 A1 | 4/2002 | Vardi et al. | |
| 2002/0143386 A1* | 10/2002 | Davila et al. | 623/1.15 |
| 2002/0156516 A1 | 10/2002 | Vardi et al. | |
| 2002/0173835 A1 | 11/2002 | Bourang et al. | |
| 2003/0083734 A1* | 5/2003 | Friedrich et al. | 623/1.15 |
| 2003/0144725 A1* | 7/2003 | Lombardi | 623/1.13 |
| 2003/0187494 A1 | 10/2003 | Loaldi | |
| 2003/0195606 A1 | 10/2003 | Davidson et al. | |
| 2003/0219562 A1* | 11/2003 | Rypacek et al. | 428/36.91 |
| 2004/0015227 A1 | 1/2004 | Vardi et al. | |
| 2004/0019302 A1 | 1/2004 | Williams et al. | |
| 2004/0088007 A1 | 5/2004 | Eidenschink | |
| 2004/0133268 A1* | 7/2004 | Davidson et al. | 623/1.35 |
| 2004/0138737 A1 | 7/2004 | Davidson et al. | |
| 2004/0267352 A1* | 12/2004 | Davidson et al. | 623/1.15 |
| 2005/0010278 A1 | 1/2005 | Vardi et al. | |
| 2005/0015108 A1 | 1/2005 | Williams et al. | |
| 2005/0060027 A1 | 3/2005 | Khenansho et al. | |
| 2005/0102019 A1 | 5/2005 | Yadin | |
| 2005/0288769 A1* | 12/2005 | Globerman | 623/1.15 |
| 2005/0288771 A1* | 12/2005 | Majercak et al. | 623/1.15 |
| 2006/0036315 A1 | 2/2006 | Yadin et al. | |
| 2007/0016279 A1* | 1/2007 | Konstantino et al. | 623/1.11 |
| 2007/0060888 A1 | 3/2007 | Goff et al. | |
| 2007/0073388 A1* | 3/2007 | Krolik et al. | 623/1.31 |
| 2007/0173921 A1* | 7/2007 | Wholey et al. | 623/1.13 |

FOREIGN PATENT DOCUMENTS

| | | |
|---|---|---|
| EP | 0 800 801 | 10/1997 |
| EP | 1255506 B1 | 11/2002 |
| WO | WO 00/44319 A1 | 8/2000 |
| WO | WO 03/020173 | 3/2003 |
| WO | WO 03/105695 | 12/2003 |
| WO | WO 2004/006807 | 1/2004 |
| WO | WO 2006/127125 A3 | 4/2006 |
| WO | WO 2006/127125 A2 | 11/2006 |
| WO | WO 2006/127127 A1 | 11/2006 |

OTHER PUBLICATIONS

Notice of opposition to European patent dated Feb. 9, 2012 against EP 1835866.

* cited by examiner

STENT WITH SELF-DEPLOYABLE PORTION

CROSS-REFERENCES TO RELATED APPLICATIONS

This application is a non-provisional and disclosure of this application is related to and claims the benefit of the following prior provisional applications: 60/740,935, filed on Nov. 29, 2005; 60/712,949, filed on Aug. 30, 2005; 60/684,454, filed on May 24, 2005; and 60/643,062, filed on Jan. 10, 2005, the full disclosures of which are incorporated herein by reference.

BACKGROUND OF THE INVENTION

Field of the Invention

The present invention relates to medical devices and more specifically to medical devices used in the treatment of vascular stenoses at or near a bifurcation lesion.

Stenting is a common medical procedure mainly directed at revascularization of stenotic vessels where a blocked artery is dilated and a stent is placed in the artery to maintain vessel patency following the procedure. A stent is small mesh like tubular device, usually fabricated from metal, that can be coated with a drug or a polymer containing a drug.

While stents are successful in treating a variety of lesions in the vascular system, their success is limited in the treatment of bifurcation lesions and ostial lesions. Often, during stent placement in the main vessel at a bifurcation lesion, the stent mesh blocks access to the side branch thereby disrupting blood flow patterns and limiting blood flow to the side branch. Additionally, placing a stent in the side branch of a bifurcation lesion often results in the stent protruding into the main vessel which can later interfere with stent placement in the main vessel as well as limiting branch vessel access.

In addition to acute problems such as long procedure time, complications from stents placed in bifurcation lesions can result due to the limited side branch access along with the need to use conventional stents against their intended design or labeled use. This can compromise long term results resulting in a higher rate of restenosis as compared to stenting other lesions.

One method of using conventional stents in bifurcation lesions is to deliver a first stent to the main vessel followed by delivering a second stent to the side branch through the struts of the main vessel stent. However, this procedure is difficult since the second stent can get caught while passing through the first stent. Another commonly used method is to place the side branch stent before the main vessel stent. In this case, there could be a gap between the two stents, and restenosis often occurs in this gap. Alternatively, the gap may be eliminated by delivering the side branch stent with a portion protruding into the main vessel. In this case the protruding stent will be crushed during delivery and expansion of the main vessel stent. Results of crushing the side branch stent are hard to predict and can lead to undesired deformation of the stent as well as dissection of the blood vessel.

Drug eluting stents have demonstrated clinical success in the coronary vessels but have failed so far to demonstrate similar success rates in bifurcation lesions. This outcome is attributed to the lack of metallic stent coverage in the gap between the main vessel stent and the side branch stent.

Conventional stent designs are well disclosed in the prior art. These designs comprise a number of different stent configurations and geometries along with various coatings and materials for fabrication. Stainless steel and cobalt chromium alloys are commonly used for balloon expandable stents while a nickel titanium alloy is typically employed in self-expanding stents. The use of self-expanding stents in the coronary arteries is limited however, due to the need for accurate sizing and positioning as well as because of the limited ability for post-delivery stent manipulation required for optimal stent positioning.

Attempts have been made to design a dedicated stent for bifurcation lesions. There is a need for ostial side branch support and local drug delivery to the bifurcation area via a stent coating. However, current solutions suffer from a number of shortcomings such as high profile relative to conventional stents, the need for a cumbersome delivery system to place the stent in the proper location and insufficiently accurate rotational positioning facing the side branch.

Stents with reduced profiles and improved flexibility have been designed and attempted using self-expanding stents made from superelastic materials (such as nickel titanium alloy). These stent devices do not require a balloon to expand the stent and therefore permit a reduction in profile. However, self-expanding stents are still difficult to position and deliver to a target bifurcation site. Once expanded, the nickel titanium stents are not easily manipulated with a balloon nor is post-delivery dilatation very effective.

Both balloon expandable stents and self-expanding stents for bifurcation lesions are limited in their ability to accommodate a wide range of bifurcation angles. Self-expanding Nitinol strives to achieve its pre-set configuration and thus undesired gaps might be created between the stent and the vessel wall after expansion. Also, currently available balloon expandable stents are limited in their ability to adopt the local anatomical configuration.

To overcome this problem, a "kissing balloon" technique is often used. In this technique two angioplasty balloons are simultaneously inflated in the main vessel and the side branch with the objective of obtaining good wall apposition of the stents. This technique is currently the best method available. However, the two balloons are inserted into the artery over conventional metallic guidewires that affect the local geometry at the bifurcation site and suppress the real bifurcation angle. Once the balloons and the wires are pulled out, the side branch angle is restored to its original position and this can leave a gap between the stent and the arterial wall.

For these reasons and others, the current treatment for bifurcation lesions is limited in the complexity of lesions that can be treated as well as the long term clinical benefits provided to patients. At least some of these objectives will be met by the present invention.

BRIEF SUMMARY OF THE INVENTION

The present invention provides methods and devices for the placement of a stent in a bifurcation or ostial lesion. The term "bifurcation" in this patent includes all types of bifurcation lesions and lesions near bifurcations in the vessels. The phrases "bifurcation ostium area" and "ostial lesion" apply to all types of lesions including those located at aorto-ostial and anastomosis sites.

A main body portion of a balloon expandable stent is designed to expand and support the main vessel while a flaring portion is designed to open into and support a side branch or bifurcation ostium area at least partially in response to expansion of the main body. The term "flaring portion" used in this application refers to a portion of the stent that protrudes outwardly from the stent surface after the stent has been expanded, i.e., it is no longer radially collapsed. Expansion of the flaring portion can be achieved with the use of a single balloon disposed in the main body of the stent and without the need for an additional balloon that is placed in the flaring portion.

The stent design eliminates the need for using self-expanding materials such as nickel titanium alloy and the self-deploying feature of the flaring portion is achieved due to the overall design of the stent features or the balloon features, although in some instances the present invention could use self-expanding materials in combination with the balloon expandable components.

In a first aspect of the present invention, a balloon expandable stent comprises a main body and a flaring portion. The flaring portion is designed to open at least partially in response to expansion of the main body and does not depend on direct contact with the balloon which expands the main body. The flaring portion may be disposed on a side of the main body. The flaring portion will usually comprise a plurality of wings that flare radially outward into a side branch vessel in response to expansion of the main body. The wings of the flaring portion typically flare at an angle in the range from 10 to 150 degrees relative to a central axis of the stent.

In a second aspect of the present invention, a balloon expandable stent comprises a main body and a flaring portion. The flaring portion is designed to open at least partially in response to expansion of the main body and does not depend on direct contact with the balloon which expands the main body. The flaring portion may be disposed on an end of the main body. The flaring portion will usually comprise a plurality of wings that flare radially outward onto a branch vessel ostium in response to expansion of the main body. The wings of the flaring portion typically flare at an angle in the range from 10 to 150 degrees relative to a central axis of the stent.

Flaring of the stent flaring portion in the present invention is typically achieved by a leverage mechanism. The leverage mechanism is connected between the main body and the flaring portion and therefore, as the main body expands, the leverage mechanism is also displaced. This displacement and the corresponding expansion forces are then transferred from the main body during expansion along the leverage mechanism to the flaring portion. The leverage mechanism can be a part of the stent pattern which is designed to deflect forces and lift the side portion. The leverage mechanism can also be a portion of the main stent body or a portion of the side branch support structure.

Also, the flaring portion of the stent may comprise a proximal and distal portion. The dimensions of the leverage mechanism may be modified to make it stiffer which permits greater transfer of force and displacement from the main body during expansion to the distal flaring portion. Therefore, the leverage mechanism deflects the distal portion more than the proximal portion, thereby flaring the distal portion at a greater angle than the proximal portion.

The balloon expandable stent may also comprise a therapeutic agent disposed over at least a portion of the balloon expandable stent. The therapeutic agent may be coated on the stent or sequestered in a polymeric layer or other carrier added to the balloon expandable stent. The therapeutic agent is delivered to at least a portion of the lesion, particularly the main vessel lesion, side branch lesion or side branch ostium and the therapeutic agent helps to reduce restenosis or inflammation post stent implantation.

In another aspect of the present invention, a method for delivering a balloon expandable stent comprises positioning a stent having a main body in a vessel at an ostial opening to a vessel side branch and expanding the main body. Expanding the main body causes a portion of the main body to flare, at least partially in response to expansion of the main body. This stabilizes the stent in the main vessel and deflects a portion of the balloon expandable stent into the ostial opening. The flaring portion may be disposed on a side of the main body or on an end of the main body. A therapeutic agent may be disposed over at least a portion of the balloon expandable stent. The therapeutic agent may be coated on the stent or sequestered in a polymeric layer or other carrier added to the balloon expandable stent. The therapeutic agent is delivered to at least a portion of the lesion, particularly the main vessel lesion, side branch lesion or side branch ostium and the therapeutic agent helps to reduce restenosis or inflammation post stent implantation.

DETAILED DESCRIPTION OF THE INVENTION

The present invention is a balloon expandable stent for bifurcation and ostial lesions. The word bifurcation in this patent includes all types of bifurcation lesions and lesions near bifurcations in the vessels or ostial lesions of all types including aorto-ostial and anastomosis sites.

The stent has a tubular structure and comprises a main body that is balloon expandable and is capable of supporting a main vessel. It has a portion which flares at least partially into a side branch vessel and supports the side branch ostium in response to expansion of the main body, without requiring an additional deployment balloon. An additional balloon may be used to complete the deployment if needed.

Figure 1:
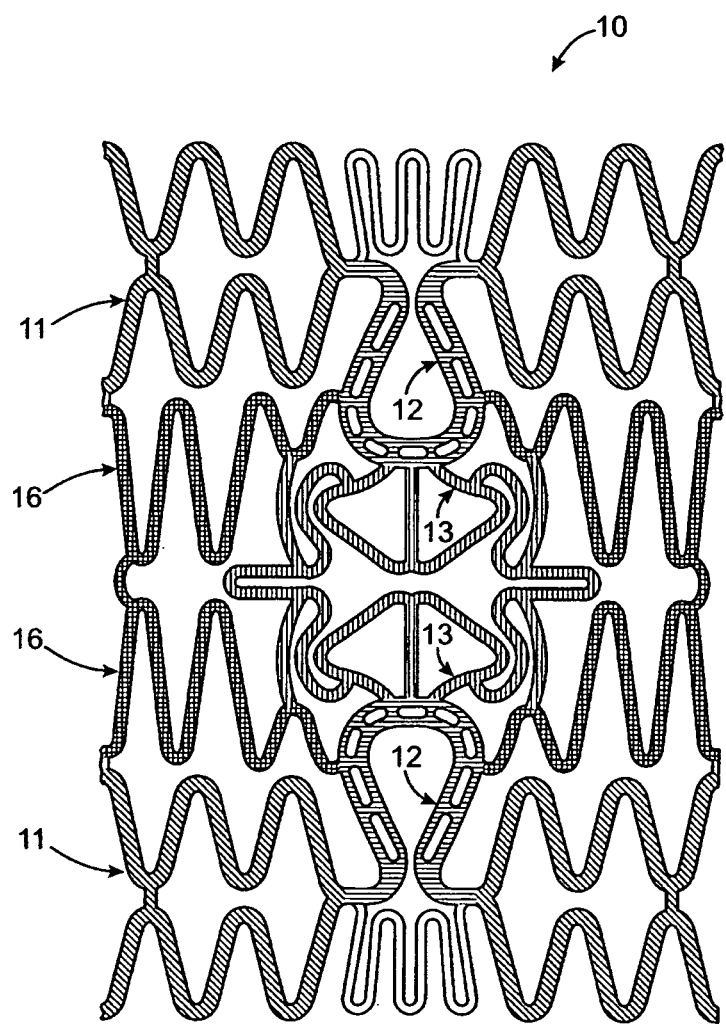
FIG. 1 shows a two-dimensional representation of a bifurcation stent, unrolled and flattened.
Figure 2:
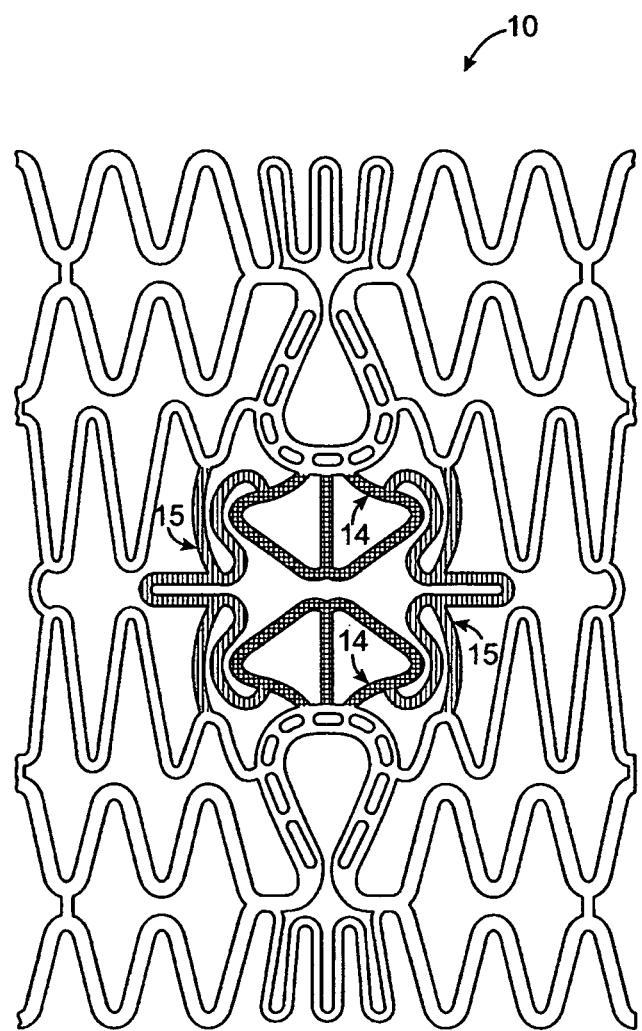
FIG. 2 shows the wings and connecting struts of the stent illustrated in FIG. 1.
Figure 3:
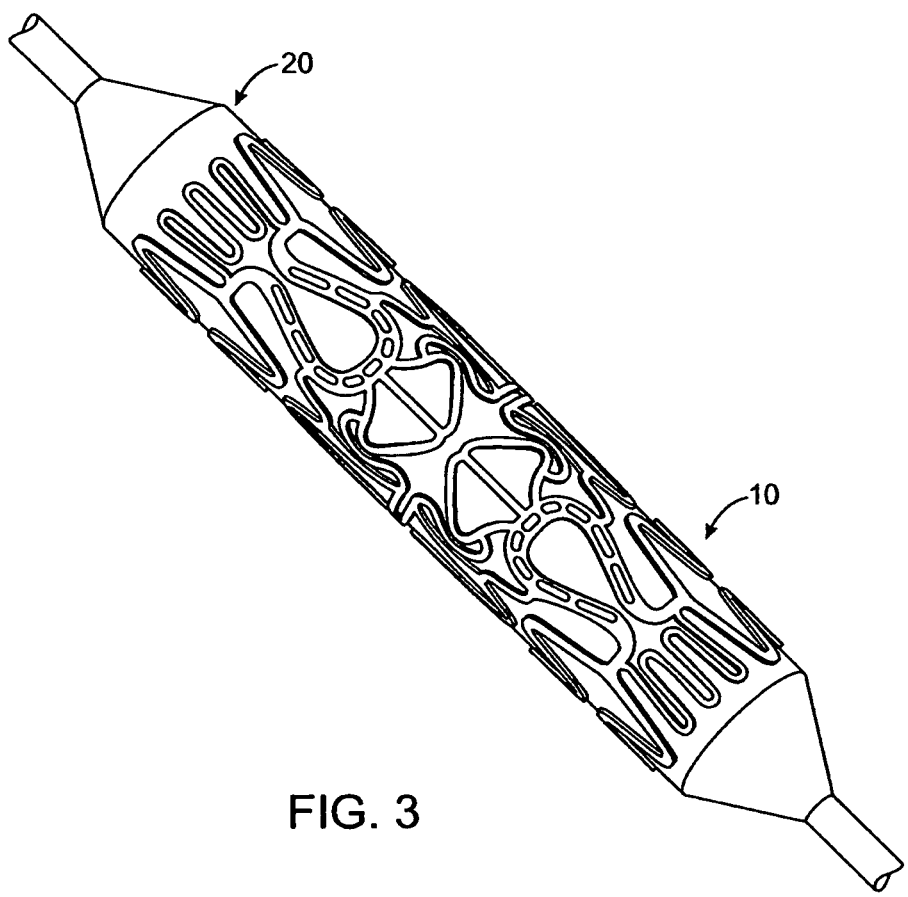
FIG. 3 shows the bifurcation stent of FIG. 1 mounted on a balloon.

An example of a bifurcation stent design 10 is shown in FIG. 1 two-dimensionally, unrolled and flattened. Additional structural features of stent 10 are also illustrated in FIG. 2 and FIG. 3 shows the same stent 10 mounted on a balloon 20. The stent 10 of FIG. 1 comprises a structure 11 designed to radially expand and a connector 12 between the radially expandable structure 11 and a flaring portion 13.

The radially expandable structure 11 is attached to both sides of connector 12 but does not necessarily form a circumferential ring. The structure 11 expands to support the main vessel while enabling the connector 12 to open. Connector 12 is designed to have a geometrical preference to deform outwardly rather than along the balloon surface. Once the expandable structure 11 expands and allows the connector 12 to open, connector 12 is deflected outwardly.

Flaring portion 13 in this example comprises two wings 14 shown in FIG. 2 that are interconnected with connecting struts 15 also shown in FIG. 2. Additional wings may be added. Alternatively, the wings can be replaced with meandering struts or any other strut design. Wings 14 are attached to connectors 12 and are deployed outwardly into the side branch when the connectors 12 deflect. The wings 14 shown in this example are symmetrical although each one can have a different size or design to allow better support of different bifurcation angles. When wings 14 are deployed, connecting struts 15 are pulled and may add more coverage to the side branch ostium. The stent further comprises another radially expandable structure 16 shown in FIG. 1 that expands due to balloon inflation and supports the main vessel at the mid-stent area. This area can be designed with many different patterns to allow coverage of the main vessel.

Figure 4:
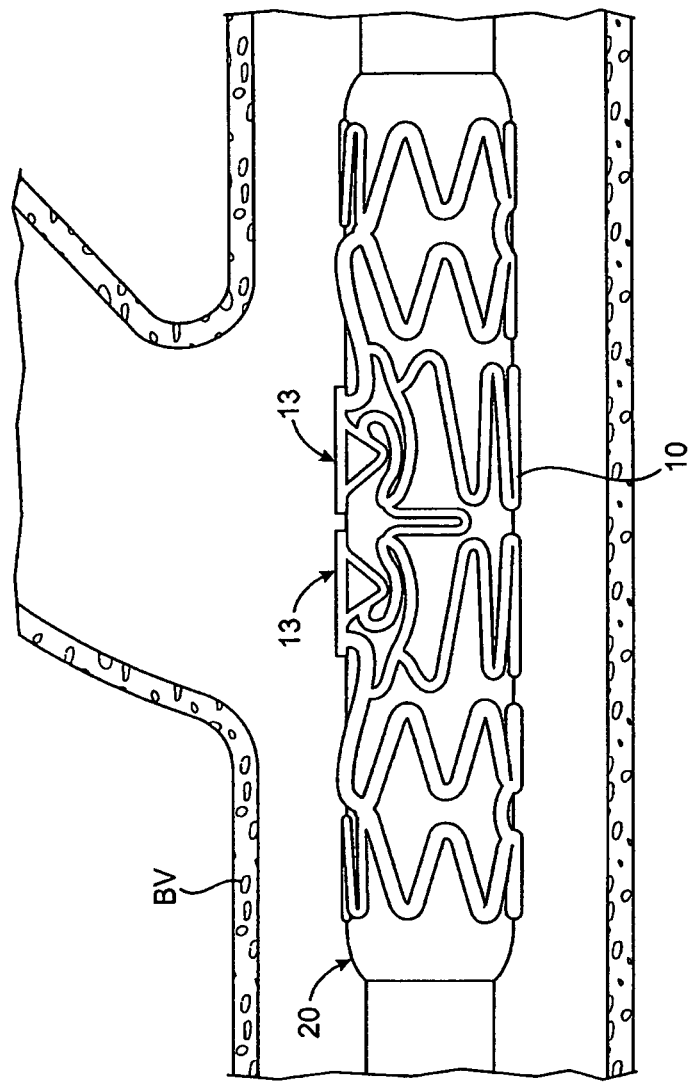
FIGS. 4-6 show the bifurcation stent at the bifurcation site before, during and after expansion.
Figure 5:
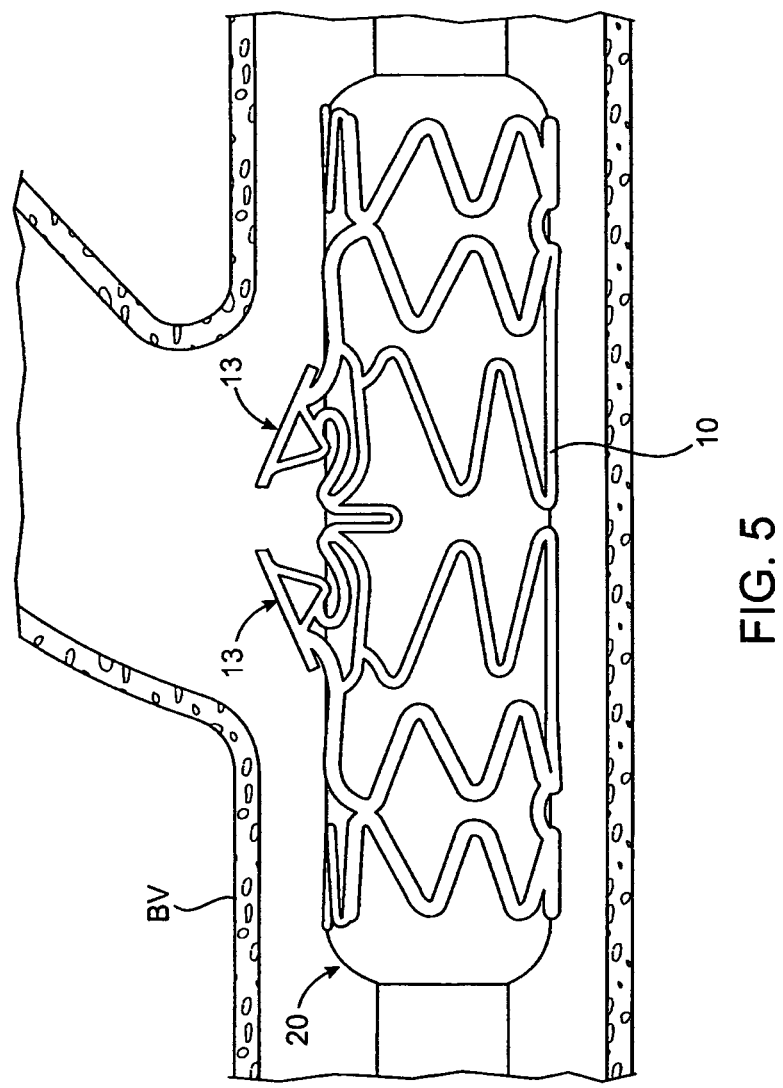
Figure 6:
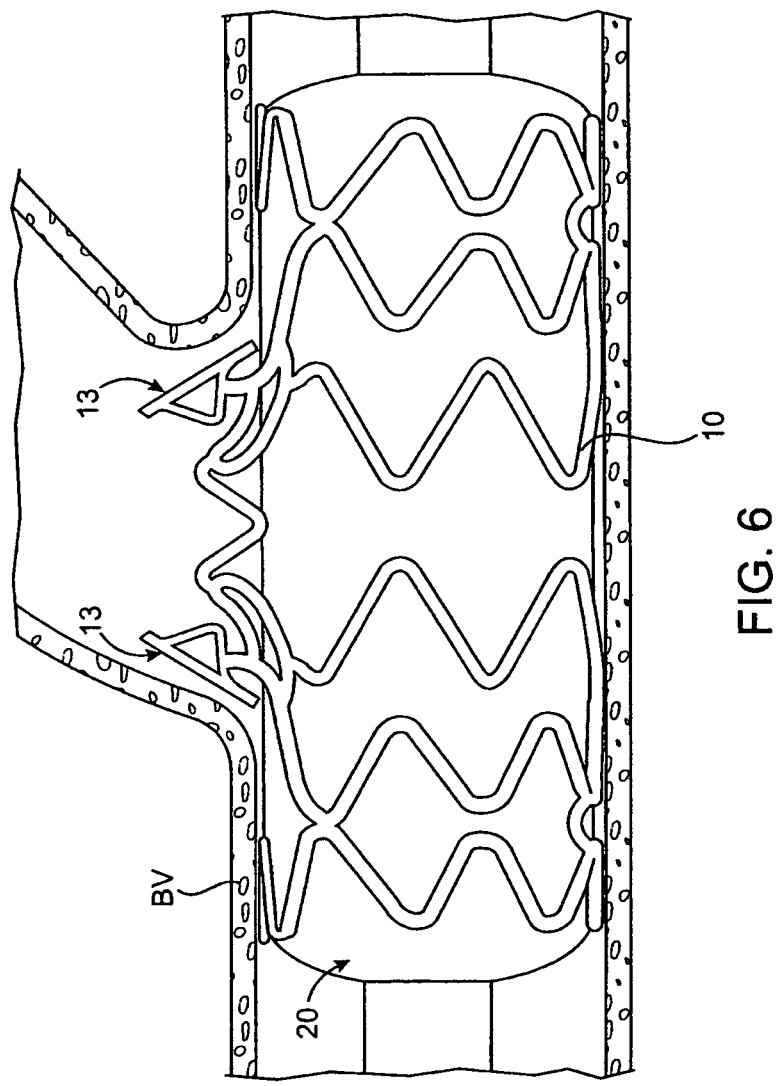
Figure 20:
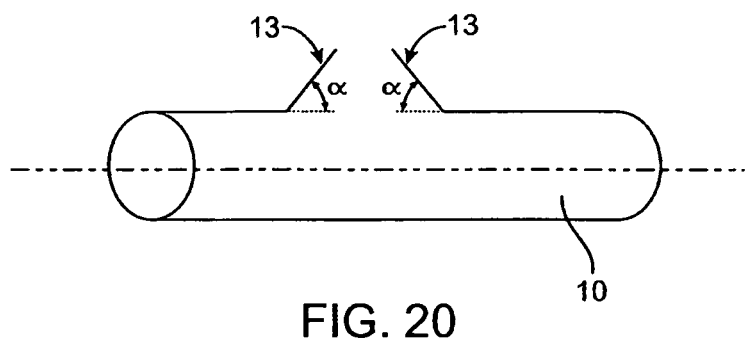
FIG. 20 illustrates the angle of the flaring portion when disposed on a side of the main body.

FIGS. 4, 5 and 6 illustrate a bifurcation stent design 10 undergoing the expansion process. FIG. 4 shows the stent 10 comprising a flaring region 13 crimped over a balloon 20 in a blood vessel (BV), FIG. 5 shows the stent during expansion where the flaring portion 13 begins to flare in response to main body expansion and FIG. 6 shows the fully expanded stent with the flaring portion 13 extending into a side branch. FIG. 20 shows α, the angle of the flaring portion relative to a central axis of the stent, which is in the range from 10 to 150 degrees, and the flaring portion is disposed on a side of the stent main body.

Figure 7:
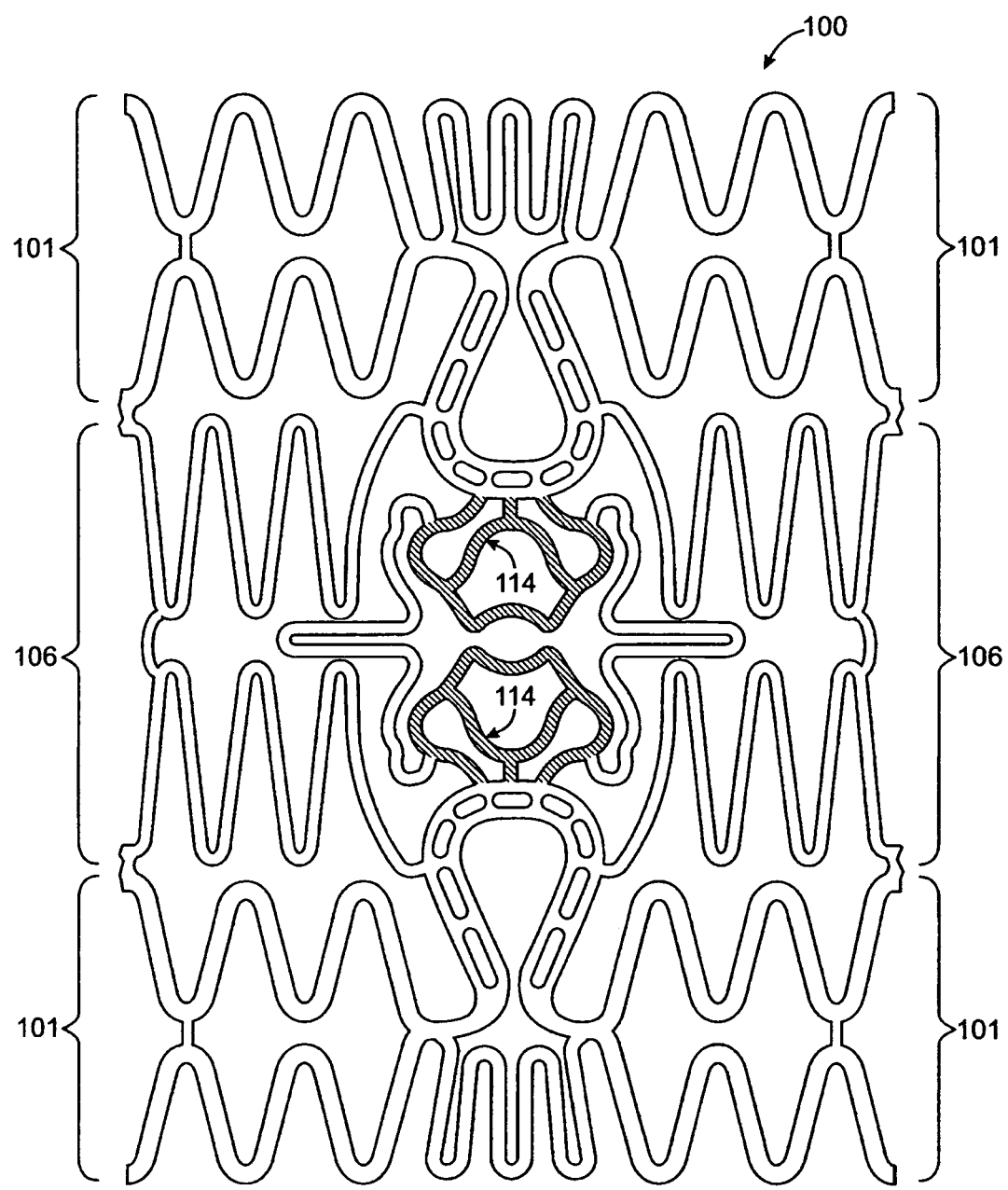
FIG. 7 shows a two-dimensional representation of another bifurcation stent design, unrolled and flattened.
Figure 9:
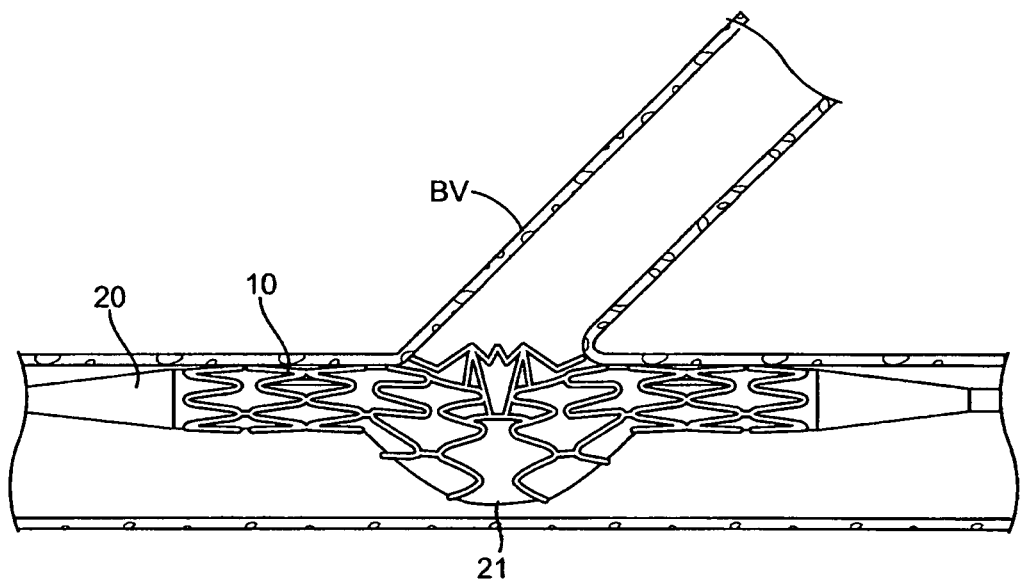
FIG. 9 shows the mid-stent area of a bifurcation stent first to expand.

FIG. 7 shows another stent design 100 containing the similar structural features as previously described in FIGS. 1 and 2, but with dimensions of structural features varied. In one embodiment the main stent body has a different stiffness near its proximal and distal ends as compared to the mid-stent region. This causes the center of the stent to expand first during deployment. Deployment of the center of the stent and the flaring portion can be achieved by altering the design of the balloon as shown in FIG. 9. One such example is a thinner balloon wall thickness closer to the center of the balloon 21. This pushes the flaring portion against the side branch ostium and it is deployed inside the side branch. Early expansion of the area near the flaring portion pushes the stent into place before deploying the flaring portion. The balloon center area design 21 can be controlled by the wall thickness, mold design or thermal treatments of the polymer.

Varying the radial stiffness of different areas of the stent can be achieved in various ways. One option is to reduce the width of struts (e.g. 106) or their thickness in the stent area that is closest to the flaring portion. Optionally, longer struts may be used when lower stiffness is desired. Another possible way is to increase the spacing between intersecting struts in areas where less radial stiffness is desired (e.g. 101, 106).

In one embodiment the flaring portion structure 13 is designed to deploy to a 90 degree angle. In another embodiment the flaring portion 13 is designed to be deployed to various pre-determined angles. In yet another embodiment the flaring portion 13 is tilted at varying angles to fit the bifurcation angle anatomy. An additional way to control the degree of flaring is by applying different inflation pressures to the main body of the balloon used for stent expansion.

In an alternative embodiment the stent is symmetrical and therefore both wings 14 of the flaring portion 13 deploy in the same way and to the same angle. Alternatively the stent 10 may not be symmetrical which causes the distal area of the flaring portion 13 to deploy at a greater angle than the proximal area of the flaring portion 13. This can be achieved by transmitting less force on the connecting strut 12 at the proximal side which in turn deflects less and therefore lifts the wing 14 to a lower angle.

An example of a way to transmit less force along the connecting strut 12 is to make the radially expandable structure 11 weaker by using radially expandable structure struts that are either longer, thinner or both. Similarly, stiffening connecting strut 12 on the distal side transmits more force and therefore deflects more thereby lifting the distal wing 14 to a greater angle than the proximal wing. Alternatively, the wings 14 may have different designs to allow for different properties and also to maximize other benefits such as selective drug delivery for example.

Figure 8:
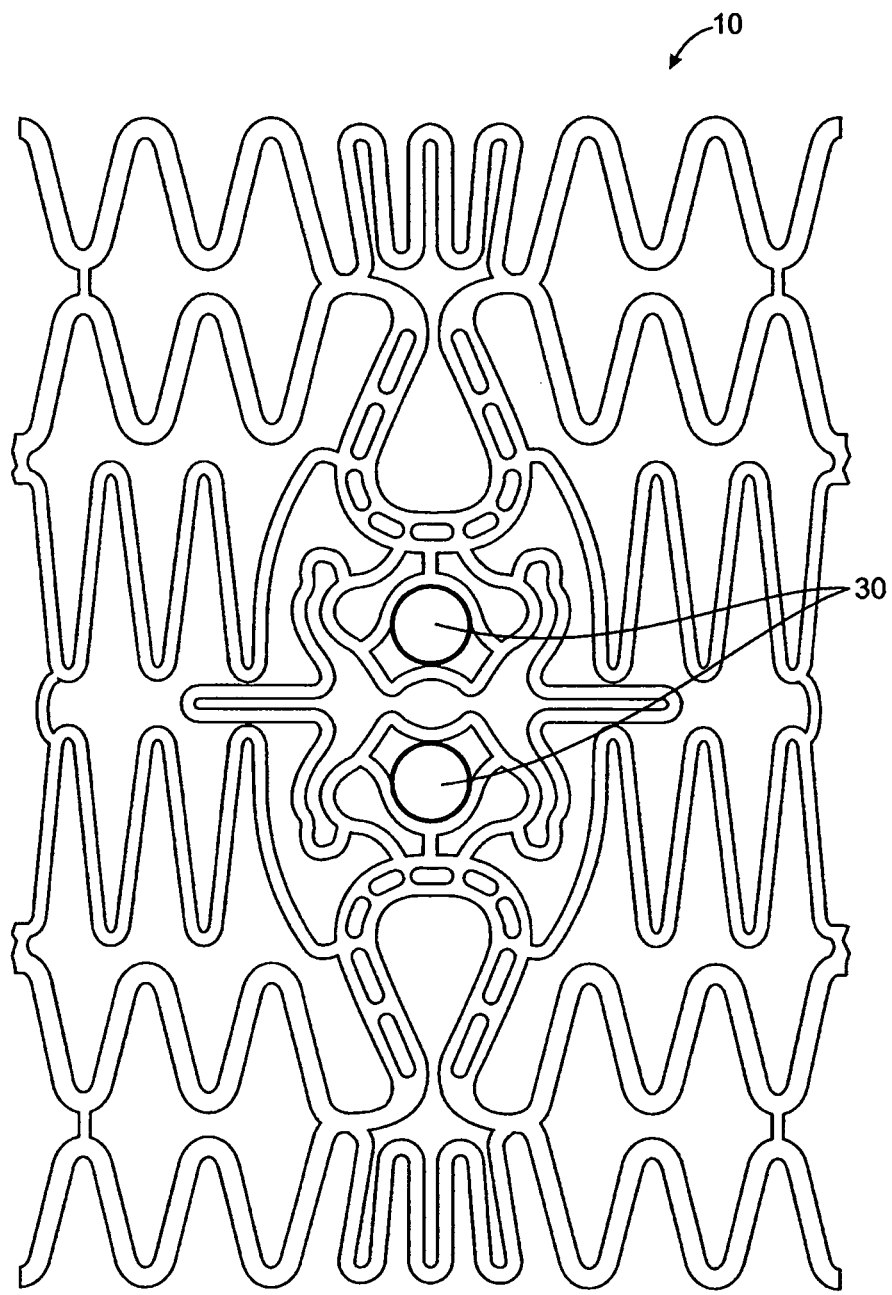
FIG. 8 shows radiopaque markers on the stent.
Figure 8A:
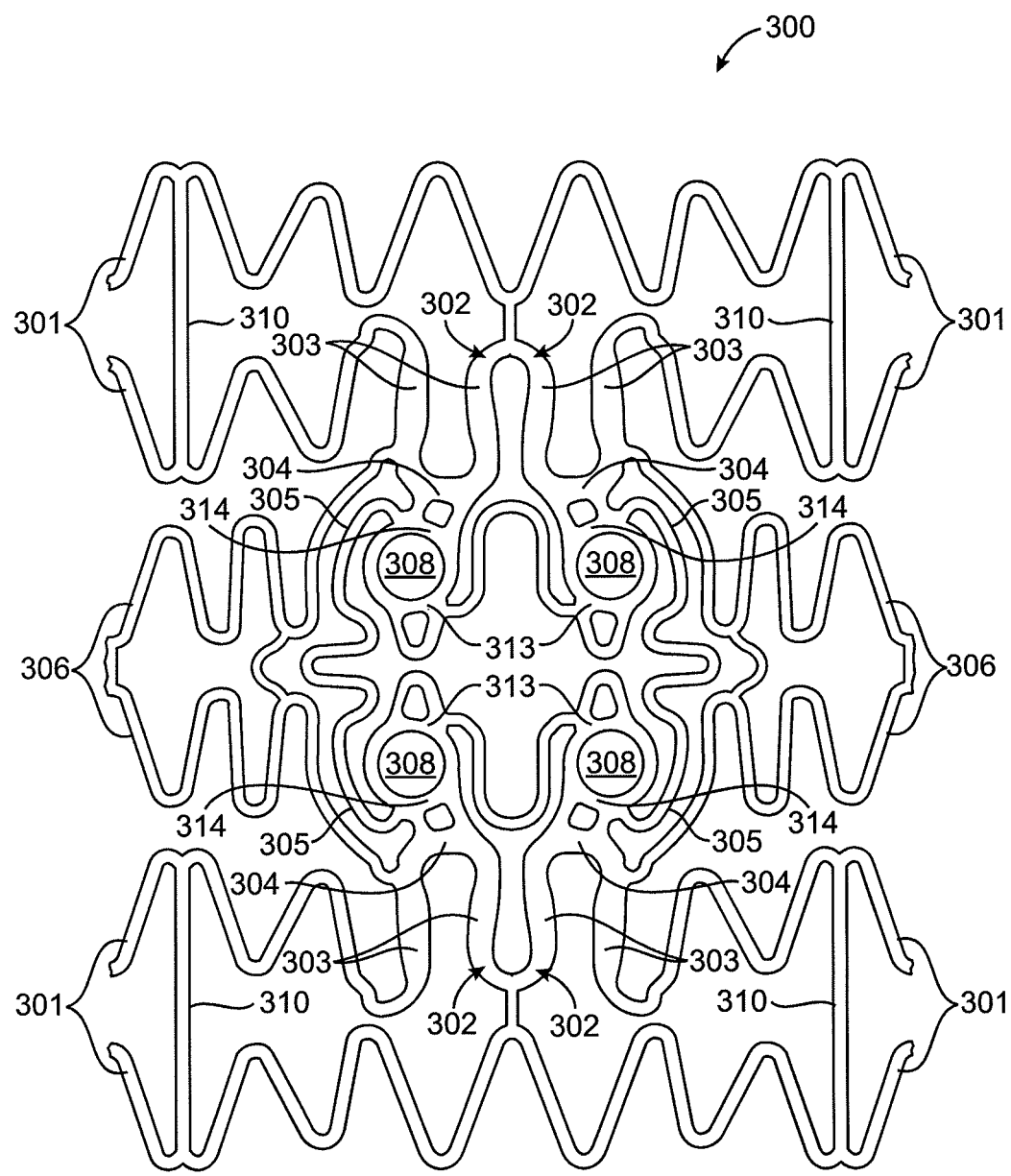
FIG. 8a shows a two-dimensional representation of another bifurcation stent design lengthened with additional connector struts and with four radiopaque markers.

In another embodiment the stent may comprise radiopaque markers to assist accurate positioning of the stent. For example, in FIG. 8, radiopaque markers (30) fabricated from radiopaque materials such as gold, platinum, tantalum and the like, can be attached to the stent 10 at different locations and can be viewed via fluoroscopy. FIG. 7 shows an example of a stent where the wings 114 of the flaring portion are designed to include a marker welded or otherwise attached to the stent. Preferred locations for these radiopaque markers are the wings 114 of the flaring portion. Having radiopaque markers placed on each of the wings 114 of the flaring portion will assist the physician in determining where the flaring portion is positioned relative to the side branch before stent expansion as well as helping to position the stent accurately. It will also enable the physician to see the flaring portion deployed into the vessel side branch. This is advantageous because not only does it help the physician to identify the side branch location but also helps in placing a second stent or re-guidewiring the side branch for post deployment treatments of the side branch area. Multiple radiopaque markers 308 may be attached to the flaring region in order to further enhance visibility as illustrated in FIG. 8a, which shows four radiopaque markers.

The stent can be made from biocompatible alloys such as stainless steel, cobalt chromium, titanium, nickel titanium alloys, niobium alloys or any other material suitable for use in body implants. The stent may further include graft materials such as PTFE or polymer membranes. The stent may be coated with an anti-inflammatory drug or other therapeutic agents with or without a polymer. The use of self-expanding materials such as nickel titanium alloys is optional but not necessary for the functionality of the stent and the self-opening of the flaring portion. The stent can be made of resorbable or absorbable materials such as different polymer formulations, magnesium alloys and other materials that are resorbable or absorbable under body conditions.

FIGS. 1 and 2 also illustrate another embodiment where the stent 10 comprises three sections, a stent main body, a flaring portion 13 and an optional leverage mechanism 12 or 15 connecting the main body and the flaring portion 13. The leverage mechanism 12 or 15 is designed to connect the flaring portion 13 and the main body in a way such that forces and displacement resulting from the partial expansion of the stent main body or the inflation of the main body balloon are transferred and utilized to expand the flaring portion 13. The leverage mechanism 12 or 15 may be integrated with the design of the flaring portion 13 or the main body to help deploy the flaring portion 13 once the main body balloon is inflated, and can be fabricated in the same way as the rest of the stent. For example, the entire stent pattern including the side portion and the leverage mechanism may be laser cut from a tube.

In yet another embodiment of the invention the main body and the flaring portion share the same pattern or same pattern features. These two portions of the stent are connected by a leverage mechanism with different design features aimed to deploy the flaring portion by leveraging the geometrical changes and forces resulting from the main body expansion.

In another embodiment the flaring portion expansion occurs before the completion of the main body expansion. In this embodiment the side branch portion expansion helps the positioning and the alignment of the stent in the bifurcation area and allows the stent system to acquire the angle of the bifurcation and comply with the local anatomy.

In one embodiment the main body of the stent has more than a single pattern. In this case the area of the stent that is close to the flaring portion has a different pattern than the areas of the stent that are further away from the flaring portion. The flaring portion may have either one of these patterns, a different pattern or no pattern at all.

In another embodiment the stent design allows the use of a delivery system with a single balloon without the need for additional means for deploying the flaring portion. In this embodiment the profile of the system can be very low as compared to other bifurcation stent systems and is typically lower than 0.06," preferably lower than 0.05" and usually lower than 0.04" which is a typical profile of conventional stents not dedicated to bifurcation lesions. This low profile can be achieved due to the design of the stent and the automatically deployed flaring portion.

In another embodiment the stent can be coated with various coatings including biocompatible oxide layers such as Ir oxide and the like, drug containing polymer coatings whether biodegradable or not, or drug molecules, that can help reduce restenosis or minimize inflammation or impact biological processes in the vessel with a beneficial outcome for the patient.

In another embodiment the stent has a crimped configuration and an expanded configuration. Usually in the crimped configuration the flaring portion is crimped with the stent but is not necessarily flush with the crimped main stent body because struts in the flaring portion are not necessarily flush with the crimped cylindrical surface of the stent. Sometimes the flaring portion can be crimped flush with the main body of the stent.

In yet another embodiment the stent has a crimped configuration and an expanded configuration, whereas in the crimped configuration the proximal and distal ends of the stent are crimped to a smaller diameter than the middle area of the stent.

Now turning to FIG. 8*a*, another embodiment is illustrated with additional radiopaque markers 308 in the flaring region and additional struts 310 which lengthen the stent body. FIG. 8*a* illustrates a bifurcation stent 300 two-dimensionally, unrolled and flattened. The stent 300 of FIG. 8*a* comprises two radially expandable circumferential ring structures 301 designed to radially expand and a U-shaped connector 302 which connects the radially expandable circumferential ring structures 301 and wings 313 which comprise the flaring portion of the stent 300. One side of each connector 302 is disposed within and forms part of the radially expandable circumferential ring structure 301 which expands to support the main vessel while causing legs 303 of connector 302 to open. Connector 302 is designed to have a geometrical preference to deform outwardly rather than along the balloon surface. Once the expandable structure 301 expands and allows the connector 302 to open, connector 302 is deflected outwardly.

A flaring portion of the stent comprises four wings 313 shown in FIG. 8*a* that are interconnected with connecting struts 305 which also flare and form part of the flaring portion. The wings 313 each have a base 314 which is attached to a cross-member 304 of each connector 302, and the wings 313 are deployed outwardly into the side branch when the connectors 302 deflect. The wings 313 shown in this example are symmetrical although each one can have a different size or design to allow better support of different bifurcation angles. When wings 313 are deployed, connecting struts 305 are pulled inward and may add more coverage to the side branch ostium.

Many delivery systems used to treat a bifurcation lesion have a side sheath or a side branch guidewire that is placed in the side branch. In most cases the side sheath or side branch wire passes beneath the proximal side of the stent and exits through the side opening of the stent. In this embodiment, the side branch sheath or guidewire passes beneath the proximal wing 313 and over the distal wing 313, which could interfere with distal wing deployment. Having four wings 313 is advantageous because it creates a space in between the wings 313 and permits the side branch catheter sheath or guidewire to be deployed into the side branch without interfering with the wings 313.

The stent further comprises another radially expandable structure 306 shown in FIG. 8*a* that expands due to balloon inflation and supports the main vessel at the mid-stent area. This area can be designed with many different patterns to allow for coverage of the main vessel.

Wings 313 have also been modified so that the stent may further comprise radiopaque markers to assist accurate positioning of the stent. For example, in FIG. 8*a*, radiopaque markers 308 fabricated from radiopaque materials such as gold, platinum, tantalum and the like, can be attached to the stent 300 on the wings 313. The markers 308 may be attached to the wings 313 by swaging, welding, or fusing, for example.

These four markers 308 are advantageous because they assist the physician in viewing the flaring portion of the stent relative to the side branch before stent expansion as well as helping to position the stent more accurately. It will also enable the physician to see the flaring portion deployed into the vessel side branch. This is advantageous because not only does it help the physician to identify the side branch location but also helps in placing a second stent or re-guidewiring the side branch for post deployment treatments of the side branch area. Additionally, having four markers on the stent enables the physician to determine the stent rotational orientation under fluoroscopy prior to stent deployment. When all four markers can be detected, this is an indication that the stent side portion is either facing the fluoroscopy screen or facing 180 degrees the other way. The physician can then torque the device and rotate it until only two markers are observed, indicating a side view, facing the ostium direction thereby confirming that the stent is properly aligned for deployment.

The basic stent design described herein results in a relatively short stent, typically six to eight millimeters long. Furthermore, the architecture of the stent can be designed to foreshorten during stent deployment and cause movement of the struts toward the bifurcation area resulting in more support to the bifurcation area.

In main vessels, the average lesion length is about 15 millimeters and most lesions are in the range of 10 to 20 millimeters. Placing a short stent at the bifurcation site often will require placing additional stents both proximally and distally to the bifurcation stent. This is difficult and undesirable since additional stents may entangle as they pass through the delivered stent. For this reason, it is desirable to add length to the stent both proximally and distally and provide stent designs that vary in length typically between 10 and 20 millimeters. An additional lengthening structure can be added to the stent symmetrically around the side portion or may be added to proximal or distal sections of the stent. This additional structure can be designed with many different geometries that support a vessel wall.

Many such geometries have been described previously. A common design for example comprises rows of sinusoidal rings that are radially collapsed prior to expansion and radially opened upon balloon expansion. These sinusoidal rings are commonly interconnected with a variety of connector designs. The connector design either allows stent foreshortening during expansion or the connector design allows stent lengthening during expansion. For example, when rows of sinusoidal rings are placed peak-to-peak and a connector joins adjacent peaks of the rows, the stent will foreshorten during expansion. On the other hand, if the adjacent rings are interconnected with a connector between adjacent valleys, the stent will lengthen during expansion. Thus, additional rows may be added to produce a stent that lengthens during expansion to compensate for foreshortening around the stent side portion and provides a length in the range of 10 to 20 millimeters.

FIG. 8a illustrates additional struts 310 which connect adjacent radially expandable structures 301 so that the stent lengthens during expansion, as describe above. FIG. 8a shows the radially expandable structures 301 symmetrical on both side of the stent 300. However, either the proximal or distal end may comprise additional radially expandable structures 301 with a strut 310 in between adjacent radially expandable structures 301 to produce varying length stents. Additionally, all of the modifications and variations discussed above for other bifurcation stents may be applied to the embodiment of FIG. 8a.

Figure 10:
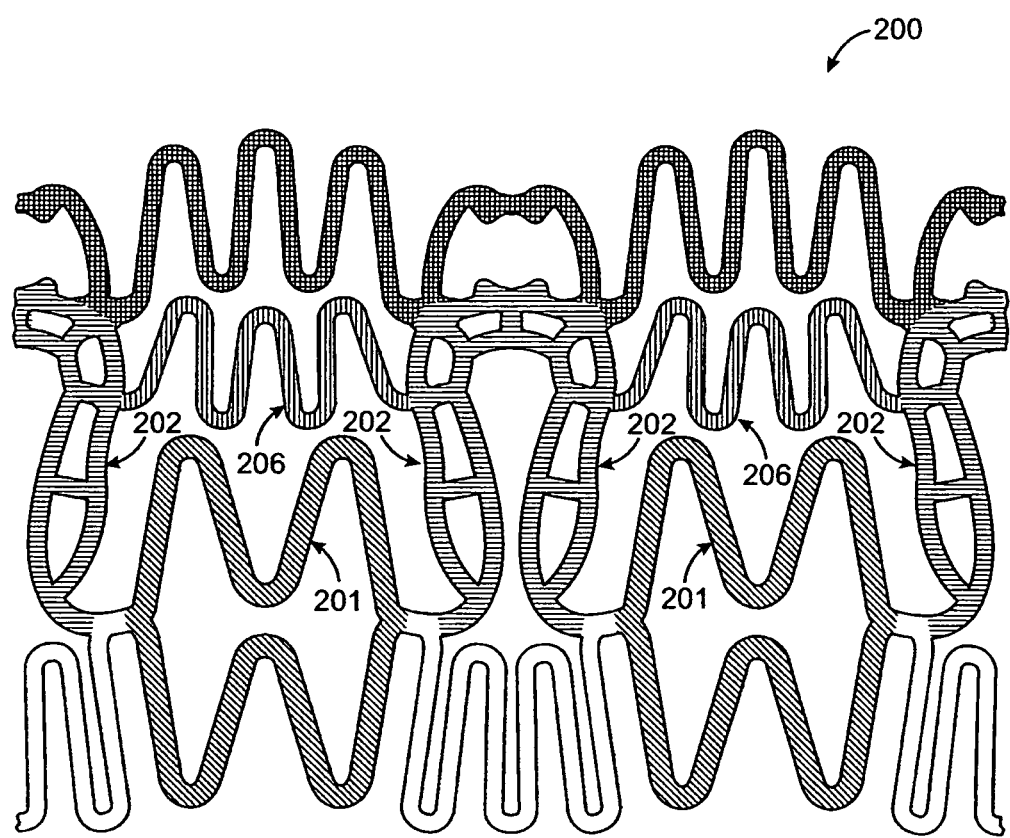
FIG. 10 shows a two-dimensional representation of an ostial stent, unrolled and flattened.
Figure 11:
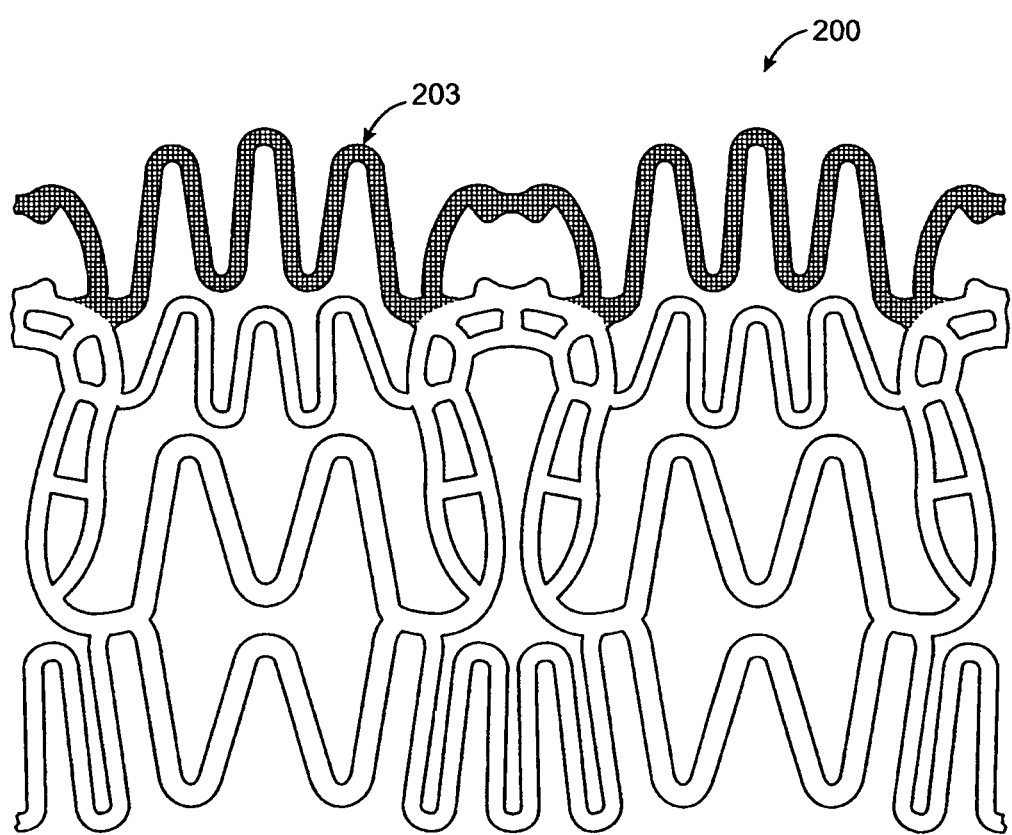
FIG. 11 shows an end portion of the stent in FIG. 10.
Figure 12:
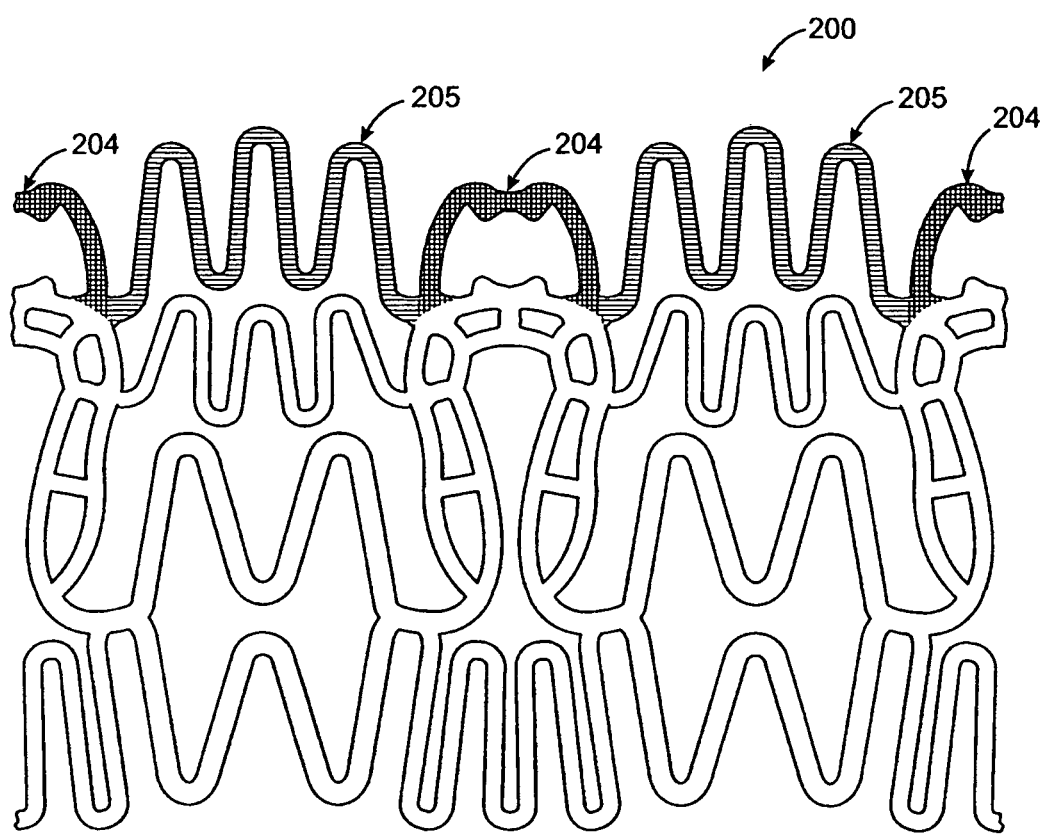
FIG. 12 shows the wings and connecting struts of the stent in FIG. 10.
Figure 13:
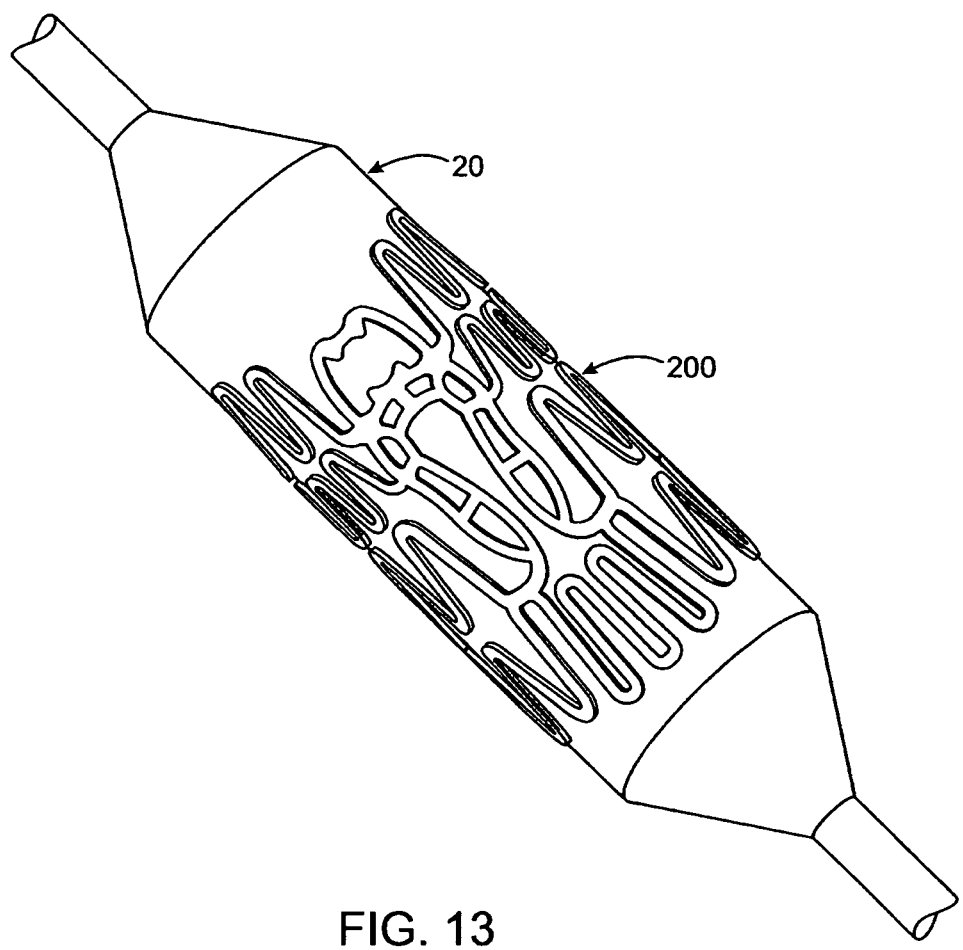
FIG. 13 shows the ostial stent of FIG. 10 mounted on a balloon.

In another embodiment the stent 200 of FIG. 10 has a crimped configuration and an expanded configuration. In the crimped configuration the proximal area of the stent is crimped to a first diameter and the distal area of the stent is crimped to a second, smaller diameter. Also, the proximal area of the flaring portion 203 is flush with the stent proximal area and distal area of the flaring portion 203 is also flush with the stent distal area. An example of such a stent design 200 is shown in FIGS. 10-13, where FIGS. 10-12 shows a two-dimensional view of the stent 200 and FIG. 13 shows the same stent 200 mounted on a balloon 20.

In another embodiment, FIGS. 10-13 describe an example of an ostial stent design 200, similar to the bifurcation design 10 previously discussed. The ostial stent design 200 comprises a structure 201 shown in FIG. 10 which is designed to expand, a connector 202 that connects between the radially expandable structure 201, and an edge portion 203 shown in FIG. 11. The radially expandable structure 201 is made of elements that do not necessarily form a circumferential ring and hang on both sides of the connector 202. The structure expands to support the side branch vessel while enabling the connector 202 to open.

Connector 202 is designed to have a geometrical preference to deform outwardly rather than along the balloon surface. Once the expandable structure 201 expands and allows the connector 202 to open, the connector 202 is deflected outwardly. The edge portion 203 comprises two wings 204 shown in FIG. 12 that are interconnected with connecting struts 205. These wings 204 are located on the connectors 202 and are deployed outwardly into the side branch ostium when the connectors 202 deflect. The wings 204 shown in this example are symmetrical although each one can have different size or design to allow better support of different bifurcation angles. An example of an alternate wing design comprises meandering struts. When the wings 204 are deployed, the connecting struts 205 are pulled and may provide more coverage to the side branch ostium.

The stent 200 further comprises another radially expandable structure 206 shown in FIG. 10 that expands due to inflation of the balloon and supports the side branch vessel at the stent area close to the ostium. This area of the stent can be designed with many different patterns to allow coverage of the side branch vessel.

In another embodiment the stent may consist an array of connectors 202 attached directly to each other without the expandable structure 201. In this case the stent 200 may include more then two connectors 202. The number of connectors may be two to six, or more.

Figure 14:
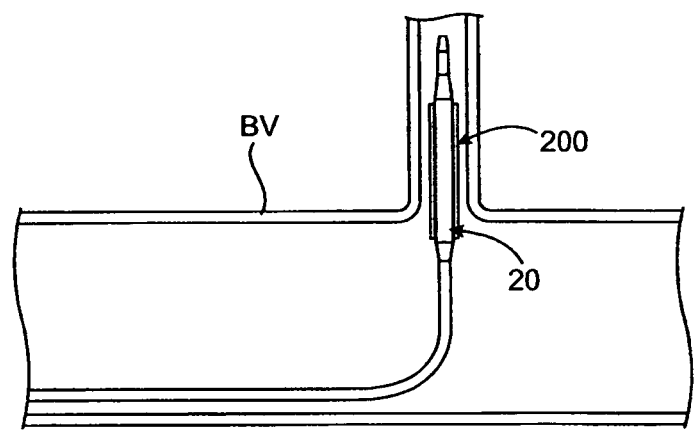
FIGS. 14-16 show an ostial stent at a bifurcation site before, during and after expansion.
Figure 15:
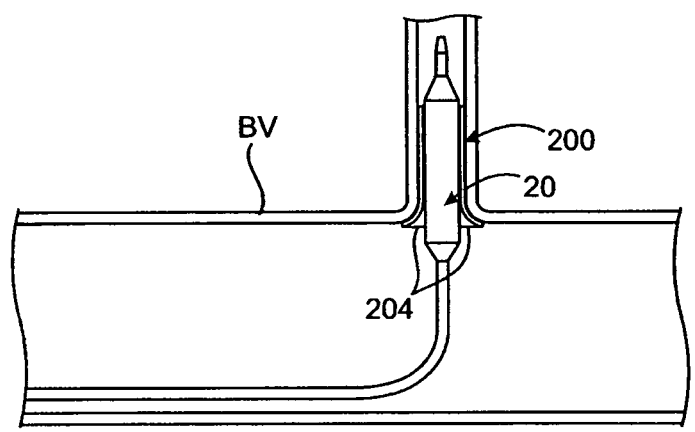
Figure 16:
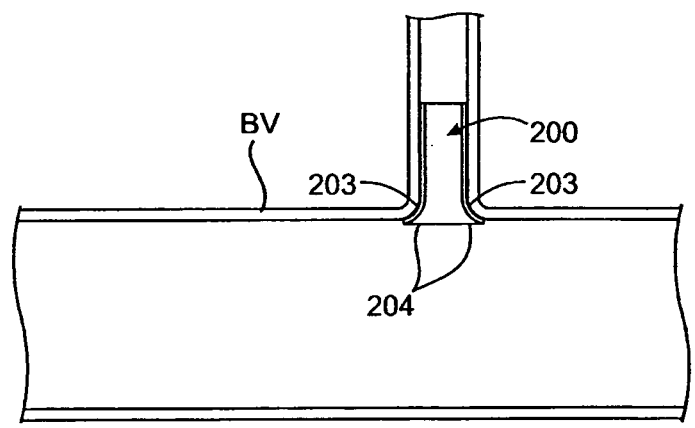
Figure 21:
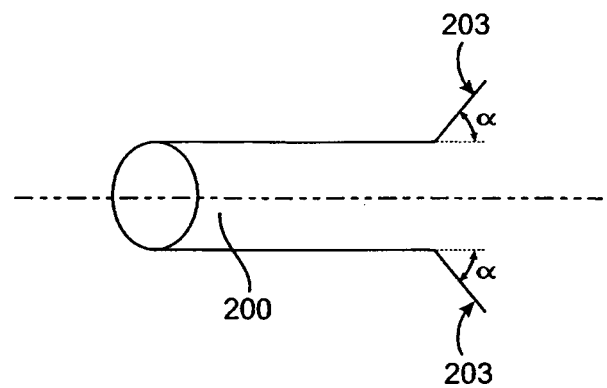
FIG. 21 illustrates the angle of the flaring portion when disposed on an end of the main body.

FIGS. 14-16 illustrate the process of ostial stent expansion. FIG. 14 shows the stent 200 crimped over a balloon 20 in a blood vessel BV while FIG. 15 shows the stent edge portion 203 deployed after the stent 200 has been expanded. FIG. 16 shows the fully expanded stent 200 after the balloon 20 is withdrawn. FIG. 21 shows α, the angle of the flaring portion relative to a central axis of the stent, and is in the range from 10 to 150 degrees. In FIG. 21, the flaring portion is disposed on an end of the stent main body.

In another embodiment the main stent body has a different stiffness near the distal end than the area of the stent closer to the ostium. This results in the stent area closer to the ostium to expand first. Deployment of the distal area of the stent and the edge portion can be achieved by altering the design of the balloon to have a larger diameter at the edge portion area. Another example is a thinner balloon wall thickness closer to the edge portion of the stent. This way the edge portion is pushed against the side branch ostium. Early expansion of the area near the edge portion pushes the stent into position before deploying the stent main body. Balloon distal area design can be controlled by the wall thickness, mold design or thermal treatments of the polymer.

Differences in the radial stiffness in different regions of the stent can be achieved by various means. One option is to reduce strut width or thickness in the stent area closest to the edge portion. Another option is to use longer struts where lower stiffness is desired. Another possible way is to increase the spacing between intersecting struts in areas where less radial stiffness is desired.

In one embodiment the edge portion structure is designed to deploy to a 90 degree angle. In another variation, the edge portion is designed to be deployed in various pre-determined angles. Optionally, the edge portion may be tilted at different angle to accommodate small bifurcation angle anatomy. An additional way to control the degree of flaring is by applying different inflation pressures to different sections of the stent with the balloon used for stent expansion.

In another embodiment the stent is symmetrical and both wings 204 of the edge portion 203 deploy the same way and at the same angle. Alternatively the stent may not be symmetrical, thus the distal area of the edge portion 203 deploys at a greater angle relative to the proximal area of the flaring portion. This can be achieved by transmitting less force on the connecting strut 202 at the proximal side which in turn will deflect less and lift the wing 204 to a lesser angle.

An example of a way to transmit less force on the connecting strut 202 is to make the radially expandable structure 201 weaker by making the radially expandable structure struts either longer or thinner or both. Similarly, stiffening connecting strut 202 on the distal side transmits more force and therefore deflects more thereby lifting the distal wing 204 to a greater angle than the proximal wing. Alternatively the wings 204 may have different designs to allow for different properties and also to maximize other benefits such as selective drug delivery for example. FIGS. 14-16 show the wings 204 opposed to one another. The number of wings can vary from one to eight wings, preferably two to four wings.

Figure 17:
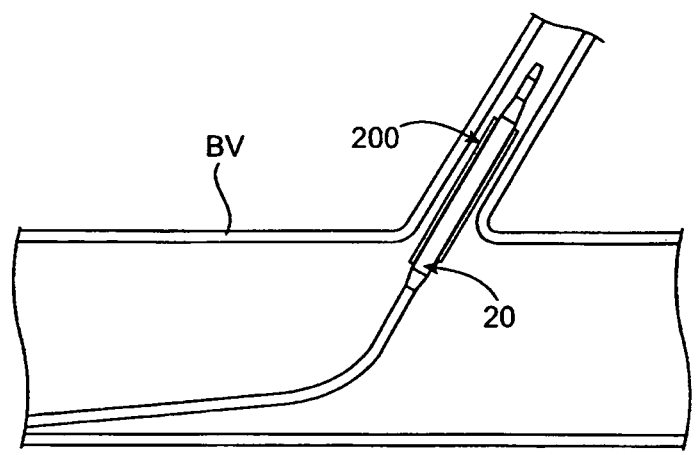
FIGS. 17-19 show an ostial stent at a bifurcation site with an angle between the branching vessels, before, during and after expansion.
Figure 18:
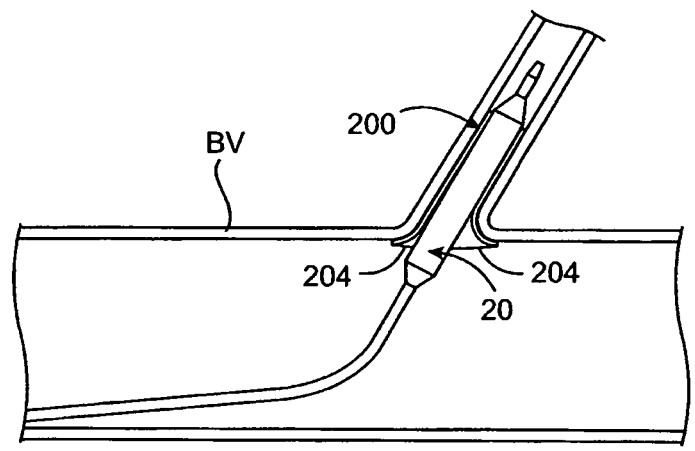
Figure 19:
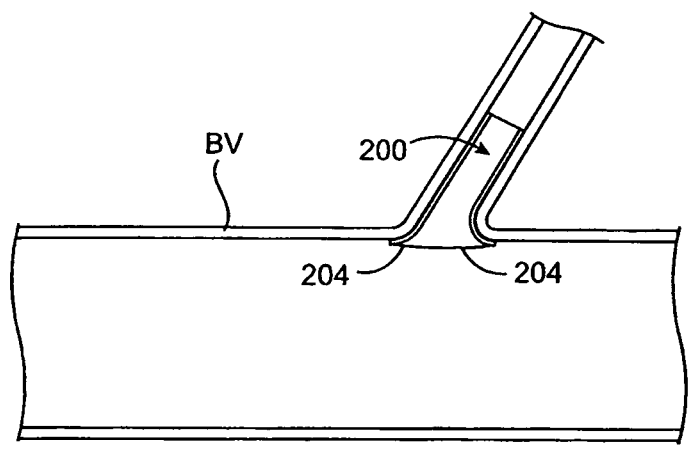

When the side branch take off angle is less then 90 degrees the ostium morphology is not cylindrically symmetrical as shown in FIGS. 17-19. In order to accommodate that morphology the stent 200 may have an angulated geometry, meaning that the crimped stent profile is cut at an angle at the proximal end (FIG. 17). The wings 204 may be gradual and asymmetrical around the stent axis, thus one wing is closer to the stent distal end than the other. When the stent 200 is deployed in the blood vessel (BV) with a balloon (20), the wings 204 comply with the ostium angulation as shown in FIGS. 17-19.

The wings can also differ in length since the distal side of the ostium is longer than the proximal side. The profile of the distal side of the ostium is different than the profile of the proximal side of the ostium. The wings can assume the same or different profiles in order to accommodate different ostial regions.

The stent may comprise radiopaque markers similar to 30 in another embodiment, to assist with accurate positioning of the stent. An example is a radiopaque marker made from radiopaque material such as gold, platinum, tantalum and the like, that can be attached to the stent at different locations and can be viewed via fluoroscopy. Preferred locations for these radiopaque markers are the wings 204 of the edge portion. Having radiopaque markers placed on each of the wings 204 of the flaring portion will assist the physician in determining where the edge portion 203 is positioned relative to the ostium before stent expansion as well as helping to position the stent accurately. It will also enable the physician to see the edge portion 203 deployed over the ostium. This is advantageous because not only does it help the physician to identify the side branch location but also helps in placing a second stent or re-guidewiring the side branch for post deployment treatments of the side branch area.

The stent can be made from biocompatible alloys such as stainless steel, cobalt chromium, titanium, nickel titanium alloys, niobium alloys or any other material suitable for use in body implants. The stent may further include graft materials such as PTFE or polymer membranes. The stent may be coated with anti-inflammatory drug or other therapeutic agents with or without a polymer. The use of self-expanding materials such as nickel titanium alloys is optional but not necessary for the functionality of the stent and the self-opening of the edge portion. The stent can be made of resorbable or absorbable materials such as different polymer formulations, magnesium alloys and other materials that are resorbable or absorbable under body conditions.

In one embodiment the stent 200 comprises three sections, a main stent body, an edge portion 203 and an optional leverage mechanism 202 or 205 connecting the main body and edge portion 203. The leverage mechanism 202 or 205 is designed to connect the edge 203 portion and the main body in a way such that forces and displacement resulting from the partial expansion of the main body or the inflation of the main body balloon are transferred and utilized to expand the edge portion 203. Alternatively the leverage mechanism 202 or 205 can be integrated with the design of the edge portion 203 or the main body to help deploy the edge portion 203 once the main body balloon is inflated, and can be fabricated in the same way as the rest of the stent. For example, the entire stent pattern including the side portion and the leverage mechanism may be laser cut from a tube.

In another embodiment of the invention the main body and the edge portion share the same pattern or same pattern features. These two portions of the stent are connected by a leverage mechanism with different design features aimed to deploy the edge portion by leveraging the geometrical changes and forces resulting from the main body expansion.

In an alternative embodiment, the edge portion expansion occurs before the completion of the main body expansion. This helps with positioning and alignment of the stent in the bifurcation area, allows the stent system to acquire the angle of the bifurcation and helps to comply with the local anatomy.

Alternatively, in another embodiment the main body of the stent has more than a single pattern. In this case the area of the stent that is close to the location of the edge portion has a different pattern than areas of the stent further away from the edge portion. The edge portion may have either one of those patterns, a different pattern or no pattern at all.

The stent design allows the use of a delivery system with a single balloon without the need for additional means for deploying the edge portion. In this embodiment the profile of the system can be very low when compared to other bifurcation or ostial stent systems and is typically lower than 0.06," preferably lower than 0.05" and usually lower than 0.04" which is a typical profile of conventional stents not dedicated to bifurcation or ostial lesions. This low profile can be achieved due to the design of the stent and the automatically deployed edge portion.

In further embodiments the stent can be coated with various coatings including biocompatible oxide layer such as Ir oxide and the like, drug containing polymer coatings whether biodegradable or not, or drug molecules, that can help reduce restenosis or minimize inflammations or impact biological processes in the vessel with a beneficial outcome for the patient.

In still another embodiment the stent has a crimped configuration and an expanded configuration. Usually in the crimped configuration the edge portion is crimped with the stent but is not necessarily flush with the crimped main body because the struts of the edge portion are not necessarily flush with the crimped cylindrical stent surface. However, the edge portion may be crimped flush with the main body of the stent. In another variation, the proximal or distal ends of the stent are crimped to a smaller diameter then the middle area of the stent.

The methods, catheters, and systems of the present invention can be utilized to deliver a wide variety of active substances, including drugs useful for treating a wide variety of luminal diseases and conditions. The methods and apparatus of the present invention are particularly useful for delivering a wide variety of therapeutic and pharmaceutical agents, referred to collectively herein as active substances, particularly those suitable for treating vascular and other luminal conditions. For example, antiproliferative and antimitotic agents such as paclitaxel or others, anti-inflammatory agents, immunosuppressive agents such as sirolimus (rapamycin) or others, antiproliferative and antimitotic antimetabolites such as folic acid analogs and any other therapeutic agent that can add benefit to the patient. The active substance may be provided on or within the stent in a variety of ways. For example, the active substance may be coated over at least a portion of an exposed surface of the stent, typically by dipping, spraying, painting, plasma deposition, electroplating, centrifuge systems or the like. More typically, however, the active substance may be incorporated in a polymeric carrier. Suitable polymeric carriers may be resorbable, such as those comprising polylactic acids (PLA), polyglycolic acids (PLG), collagens, and the like. Alternatively, the polymeric carrier may be a porous but non-resorbable material.

While the above is a complete description of the preferred embodiment of the invention, various alternatives, modifications, additions and substitutions are possible without departing from the scope thereof, which is defined by the claims.

What is claimed is:

1. A balloon expandable stent comprising:
   a main body having a plurality of radially expandable circumferential rings;
   a single flaring portion disposed on one side only of the main body and including at least a distal wing and a proximal wing, wherein each wing has a base and sides and is adapted to flare radially into a side branch;
   a U-shaped connector disposed between the main body and each wing, wherein the connector includes two legs and a cross-member where the legs are attached within one of the circumferential rings of the main body and the cross-member is attached to the base of one of the wings, the legs of said connector opening circumferentially where attached to the circumferential rings in response to expansion of the circumferential rings of the main body to cause the cross member to deform to cause the wing to flare radially; and
   struts extending from each side of the distal wing and the proximal wing to the main body, wherein the struts open with the distal wing and the proximal wing to provide coverage of a side branch ostium when each wing is opened into said ostium.

2. The balloon expandable stent of claim 1, wherein the flaring portion consists of two wings aligned axially on the main body.

3. The balloon expandable stent of claim 1, wherein the wings each flare at an angle in the range from 10 to 150 degrees relative to a central axis of the main body of the balloon expandable stent.

4. The balloon expandable stent of claim 1, wherein the connector transfers displacement and expansion forces from the main body during expansion to the flaring portion.

5. The balloon expandable stent of claim 1, wherein the wings each comprise a radiopaque marker disposed above the base and between the sides.

6. The balloon expandable stent of claim 1, further comprising a therapeutic agent disposed over at least a portion of the balloon expandable stent.

7. The balloon expandable stent of claim 6, further comprising a polymeric layer, wherein the therapeutic agent is sequestered in the polymer layer.

8. The balloon expandable stent as in claim 1, wherein the wings have different lengths.

9. A method for delivering a balloon expandable stent comprising:
   positioning a stent having a main body and a flaring portion including at least one wing on a side of the main body in a vessel at an ostial opening to a vessel side branch, wherein the flaring portion is attached to the main body by a U-shaped connector with two legs and a cross-member which is attached to a base of the at least one wing; and
   inflating a balloon within the main body but not within the flaring portion to radially expand the main body so that the legs are circumferentially opened to deform the cross-member to cause the wing to flare into the ostial opening at least partially in response to expansion of the main body, wherein struts on a side of the wing are pulled into the ostium to provide additional coverage into the ostial opening.

10. The method of claim 9, further comprising providing a therapeutic agent disposed over at least a portion of the balloon expandable stent.

11. The method of claim 10, further comprising providing a polymeric layer, wherein the therapeutic agent is sequestered in the polymeric layer.

* * * * *